United States Patent [19]

Adhoute

[11] Patent Number: 5,571,081
[45] Date of Patent: Nov. 5, 1996

[54] PER-OPERATIONAL AUTOTRANSFUSION SUCTION DEVICE

[76] Inventor: Gérard Adhoute, Domaine du Dramont, Le Dramont, 83700 Saint-Raphael, France

[21] Appl. No.: 182,098

[22] PCT Filed: May 12, 1992

[86] PCT No.: PCT/FR92/00420

§ 371 Date: Jul. 5, 1994

§ 102(e) Date: Jul. 5, 1994

[87] PCT Pub. No.: WO92/20380

PCT Pub. Date: Nov. 26, 1992

[30] Foreign Application Priority Data

May 13, 1991 [FR] France ................................. 91 05760

[51] Int. Cl.⁶ ............................................................ A61M 37/00
[52] U.S. Cl. ........................... 604/4; 604/902; 604/30; 604/269
[58] Field of Search ............................. 604/4, 119, 246, 604/269, 22, 30, 31, 33, 902

[56] References Cited

U.S. PATENT DOCUMENTS

| | | | |
|---|---|---|---|
| 3,964,484 | 6/1976 | Reynolds et al. | |
| 4,062,360 | 12/1977 | Bentley . | |
| 4,540,406 | 9/1985 | Miles | 604/269 |
| 4,921,477 | 5/1990 | Davis | 604/22 |
| 5,013,300 | 5/1991 | Williams | 604/119 |
| 5,203,769 | 4/1993 | Clemen et al. | 604/32 |
| 5,411,472 | 5/1995 | Steg et al. | 604/4 |

FOREIGN PATENT DOCUMENTS

| | | |
|---|---|---|
| 0400518 | 12/1990 | European Pat. Off. . |
| 1511671 | 12/1967 | France . |

*Primary Examiner*—David H. Willse
*Assistant Examiner*—Mark O. Polutta
*Attorney, Agent, or Firm*—Sughrue, Mion, Zinn, Macpeak & Seas

[57] ABSTRACT

A per-operational autotransfusion suction device has a suction cannular 1 with a tabular section nozzle 5, communicating with an inner passage 6, 9 in the cannula, the cannula passage being connected to a blood collecting recipient 41 in which a partial vacuum can be created by a vacuum source, the cannula passage communicating with an anticoagulant supply circuit having an anticoagulant feed control valve 15. The device has an independent vacuum circuit for sucking in only air and is connected to the vacuum source 40, to the blood collection recipient and to the valve. The valve has a vacuum chamber connected to a vacuum circuit 13, the vacuum chamber 49 having a deformable wall connected to a stopper which can close the anticoagulant feed circuit, the stopper being biased towards a closed position by a spring and capable of being biased towards an open position by deformation of the deformable wall when the pressure in the vacuum chamber is sufficiently low. The vacuum circuit communicates with an air vent 14 which can be shut off manually.

12 Claims, 5 Drawing Sheets

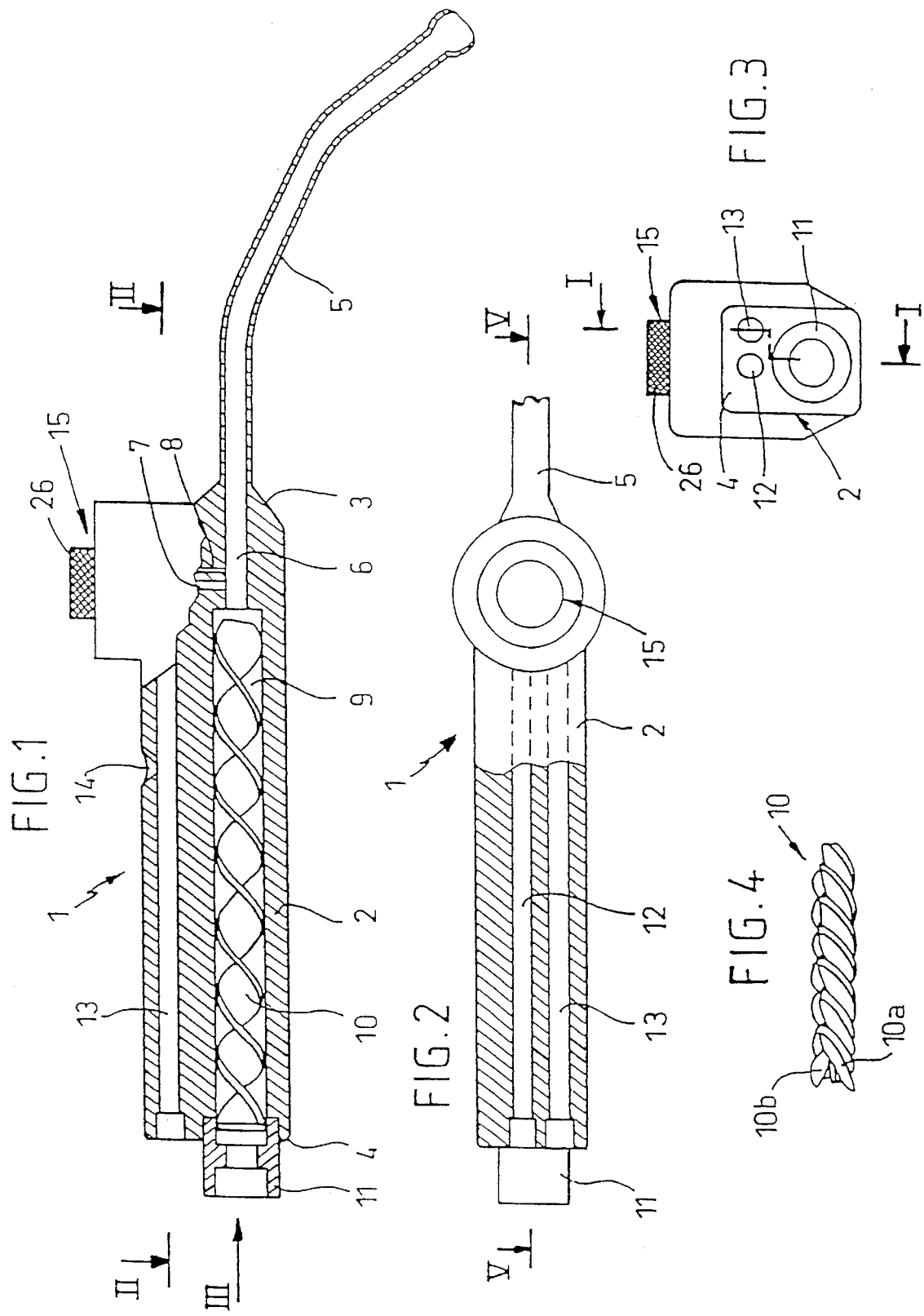

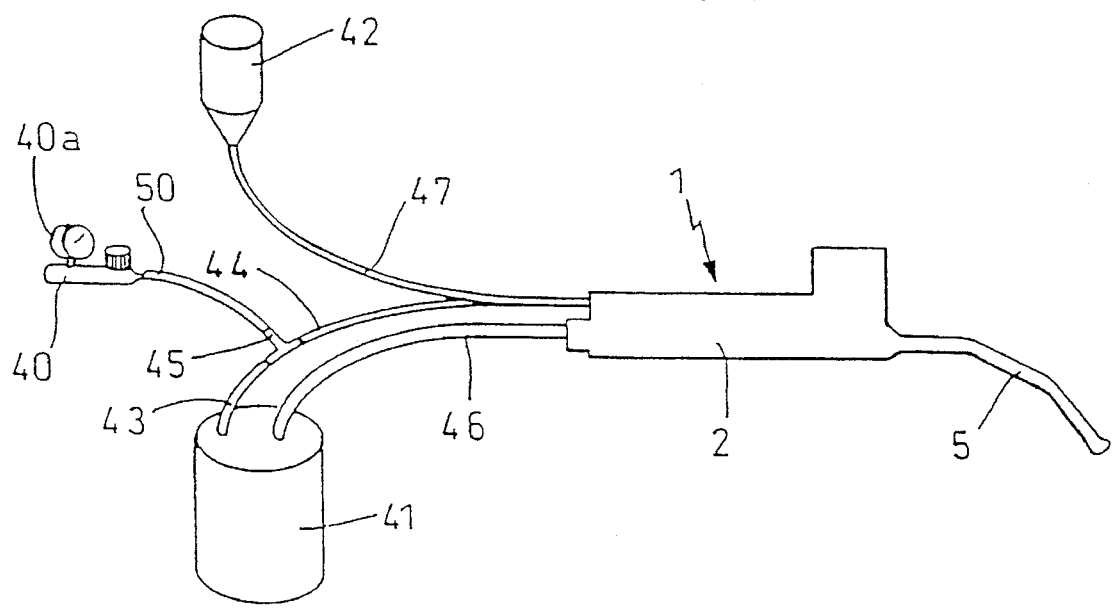
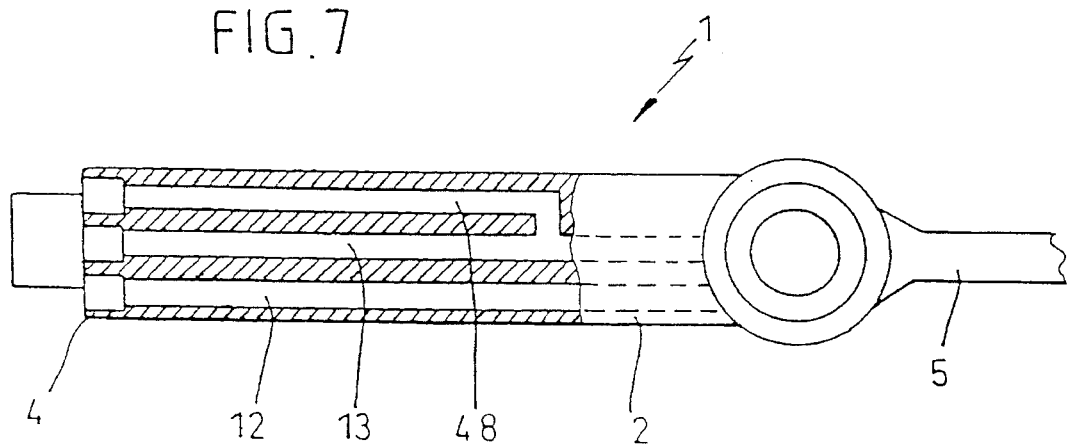

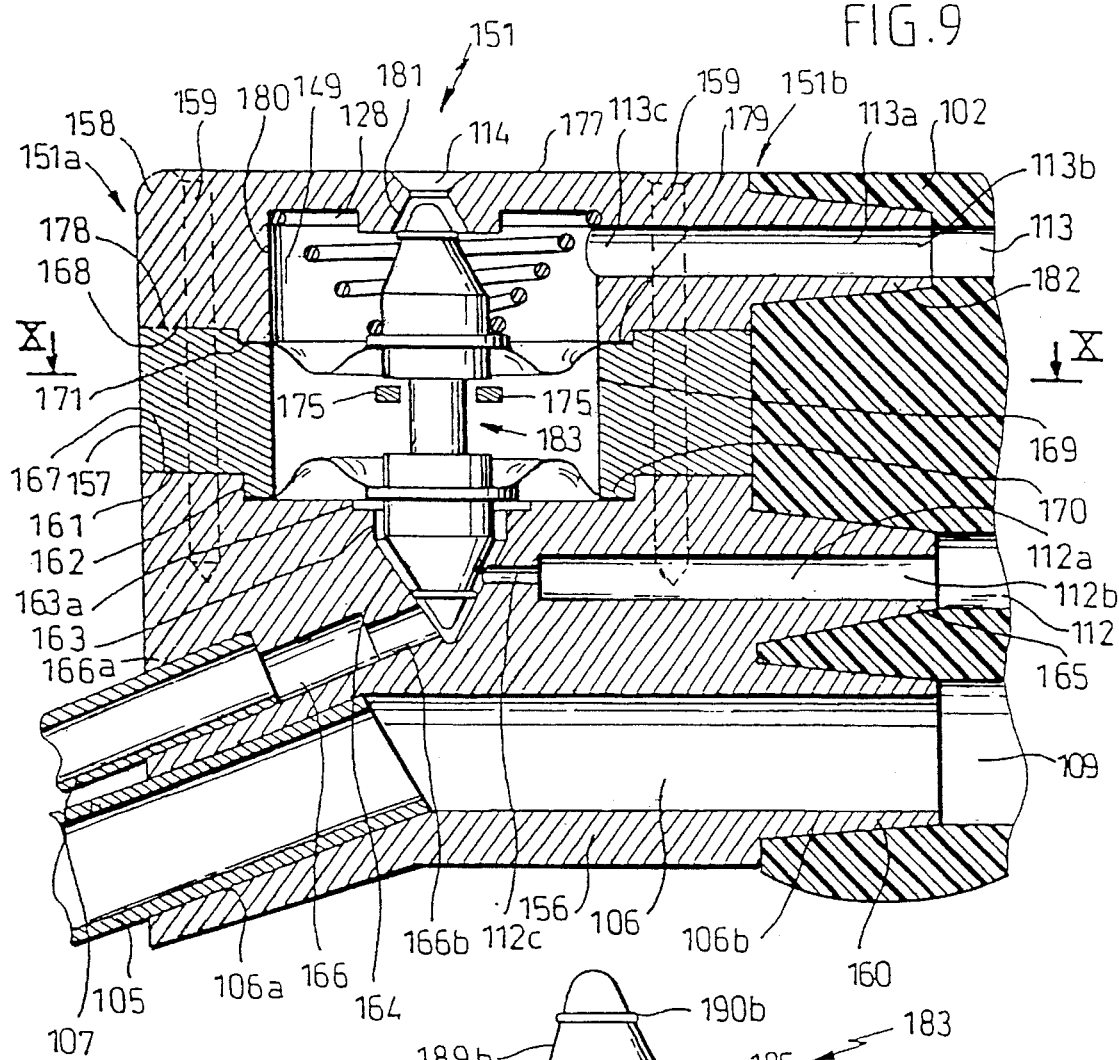
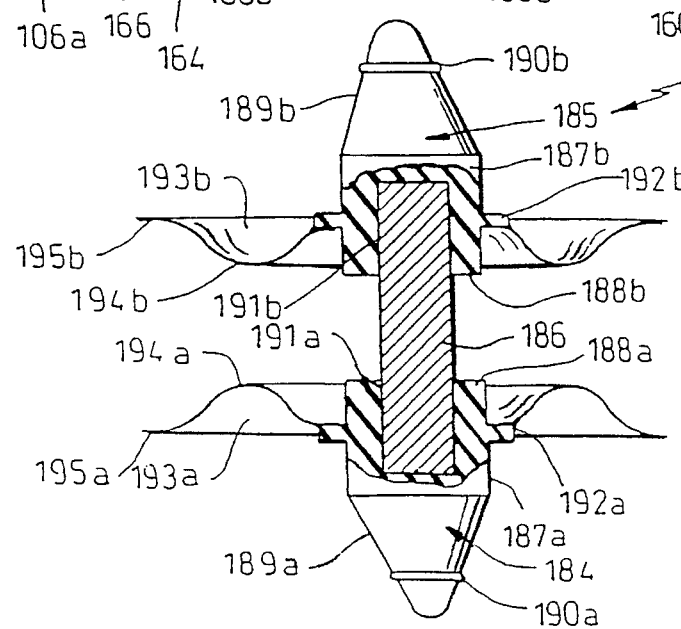

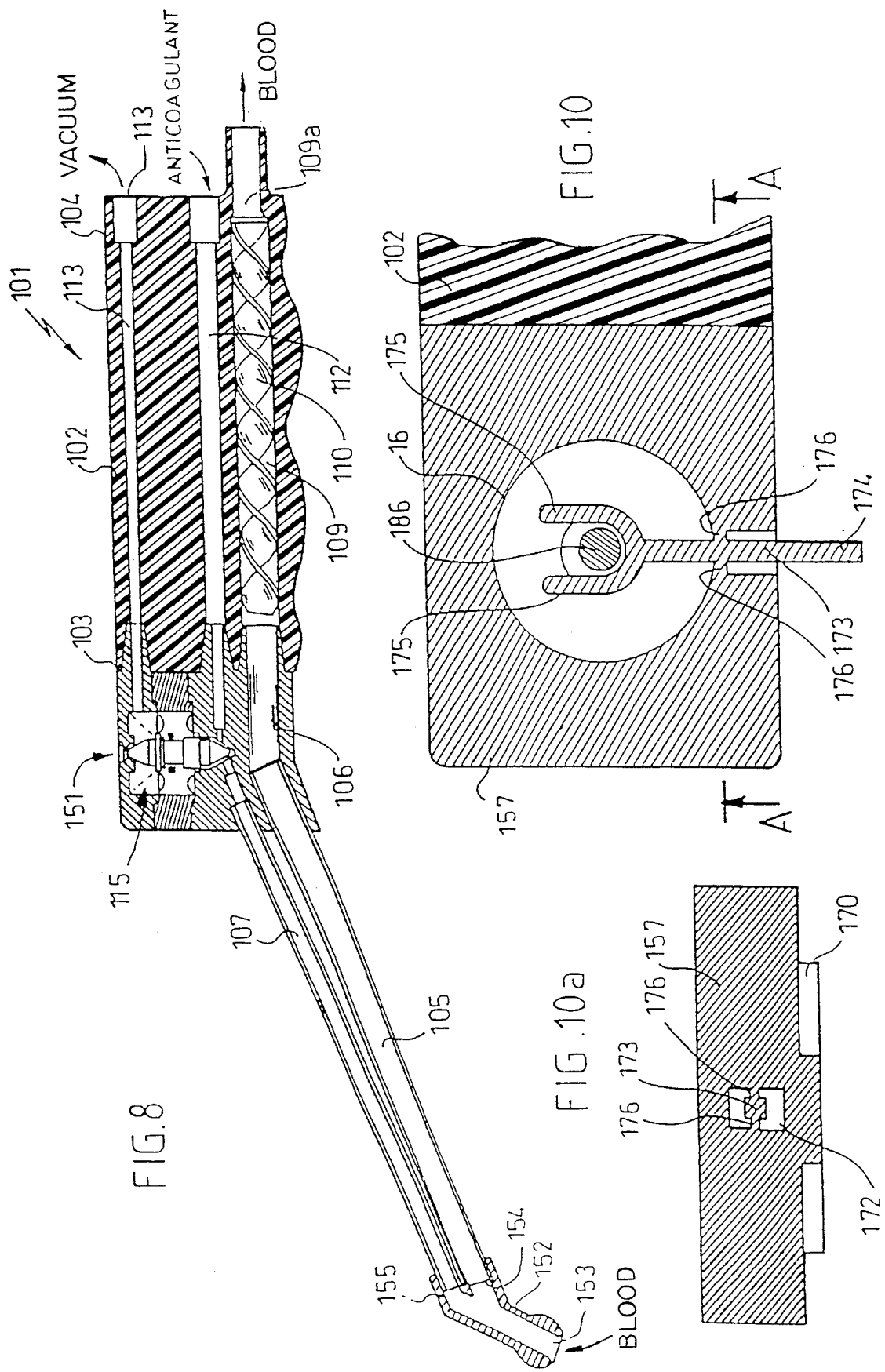

PER-OPERATIONAL AUTOTRANSFUSION SUCTION DEVICE

BACKGROUND OF THE INVENTION

This invention concerns a suction device for autotransfusion of blood during surgery.

Homologous blood transfusions, i.e. the transfusion of compatible blood from other persons, involves some risk of the transfer of illnesses such as hepatitis and AIDS. They can also cause immunodepression and reduce the patient's natural defences. Finally, some patients refuse to receive the blood of other persons because of their religious beliefs.

For these reasons autologous transfusion or autotransfusion is widely used, i.e. transfusion of the patient's own blood. Autotransfusion can be delayed in the sense that blood is taken from the patient and stored for subsequent transfusion into the same person. This is not always possible, however; the transfusion may be required urgently, for example. In this case autotransfusion during surgery can be used, in which blood lost by the patient during a surgical procedure is collected and transfused into the patient.

The device conventionally used for autotransfusion during surgery includes a suction canula connected by a flexible tube to a depressurised blood storage vessel. The suction canula is also connected to an anticoagulant storage vessel. During the surgical procedure blood lost by bleeding in the operative field is aspirated by the canula, mixed with the anticoagulant in the canula and collected in the storage vessel from which it is transfused into the patient.

A basic technical problem encountered with autotransfusion during surgery is to mix the blood and the anticoagulant in proportions that lie within the correct range. With anticoagulants such as CPD (citrate-phosphate-dextrose), for example, or heparin or a mixture of heparin and CAD (citric acid-dextrose), where a typical anticoagulant solution for 1 liter of blood serum comprises 60 ml of AB 16 plus 30 000 units of heparin, the ratio of the volume of anticoagulant to the volume of blood collected has to be around 1:7, the optimum ratio, and must not exceed 1:5 or fall below 1:10. If the ratio is too high the composition of the blood is too severely changed for the blood to be transfused while if it is too low there is insufficient anticoagulant in the mixture to prevent the blood from coagulating. At a ratio of around 1:7 the chemical, enzyme and blood corpuscle morphology composition of the blood are only slightly altered and the concentration of the anticoagulant is sufficient to prevent coagulation. With other anticoagulants the range of permissible values for the ratio of the volume of anticoagulant to the volume of blood can be different.

General information on autotransfusion can be found in the following publications:

—ADHOUTE, NAHABOO, LANCELLE, MORA, ROUVIER—Autotransfusion en pratique chirurgicale. *J. Chir.* 1977, 114, 17–24, —ADHOUTE, NAHABOO, LANCELLE, MORA, ROUVIER—Autotransfusion: XIIIth World Congress of the International Cardiovascular Society. 30 August 30 September 20, Tokyo, Japan.

—ADHOUTE, NAHABOO, REYMONDON, ORSONI—Application de l'autotransfusion en chirurgie vasculaire réglée, *Lyon Chir.*, 1978, 74, 50–62, —ADHOUTE, NAHABOO, LANCELLE, MORA, ROUVIER, BLEYN, ORSONI—Autotransfusion in Surgical Practice, Cardio. Vasc. Res. Center Bull, 1979, 18, 40–15, Texas Medical Center, Houston, Tx. 77030—USA, —ADHOUTE, HENIN—Economie du sang en chirurgie. *J. Chirurgie,* Paris, 1980, 117, 713–722.

—AUTOTRANSFUSION: Proceedings of the First International Autotransfusion Symposium: Apr. 24–25, 1980, Blood Bank Laboratories, University of Maryland School of Medicine, Md. U.S.A. Elsevier/North Holland, N.Y., Amsterdam, Oxford, —ADHOUTE, AYOUB, REYMONDON, GAUTHIER—Autotransfusion peroperatoire d'hémop éritoines en Chirurgie traumatique d'urgence: *J. Chir.,* Paris, 1988, 123, N 2, pp. 92–96, Masson, Paris, 1988, —ADHOUTE—Autotransfusion: Utiliser son propre sang. Springer-Verlag France, 26 rue des Carmes, Paris, 1989.

—ADHOUTE—Autotransfusion: using your own blood. Springer-Verlag, Heidelberg, Federal German Republic, 1991.

A solution to the technical problem of controlling the concentration of anticoagulant in the aspirated blood is proposed in French patent application No 2 503 566. This document describes a suction canula for autotransfusion during surgery with a suction nozzle at one end and the opposite end connected by a flexible tube to a blood storage vessel depressurised by a vacuum source. A tube connected to an anticoagulant solution storage vessel opens into the canula near the suction nozzle: thus if the suction nozzle aspirates air the pressure drop in the canula at the anticoagulant entry is too small for anticoagulant to be aspirated; however, if the suction nozzle is immersed in blood in the operative field the suction of this blood causes a greater pressure drop in the canula and anticoagulant is therefore aspirated into it. The dimensions of the anticoagulant feed tube as compared to those of the suction nozzle are such that the ratio of the anticoagulant to the volume of aspirated blood is approximately 1:7. However, when the canula is not being used to aspirate blood it continues to aspirate air and may therefore aspirate lightweight materials around the operative field (the gown of a person near the operative field, for example) which could block the suction nozzle: the pressure drop in the canula is then increased with the result that anticoagulant is aspirated but no blood. The same thing can happen during the suction of blood if any debris obstructs the suction nozzle and the user does not notice right away. If debris enters the suction nozzle of the canula the user may not be able to remove it quickly, in which case the vacuum source will have to be switched off to stop the flow of anticoagulant. In the meantime a relatively large quantity of anticoagulant may have been aspirated into the blood storage vessel with the result that the blood in it may be unfit for use. Also, when the canula is not aspirating blood it continues to aspirate air which then enters the blood storage vessel before it is aspirated therefrom by the vacuum source. Dust or microorganisms in suspension in the air can then collect in the blood or in a filter of the storage vessel so that the latter is no longer sterile. Furthermore, this constant flow of air in contact with the blood in the storage vessel is a source of haemolysis: the blood transfused into the patient is then lacking in red corpuscles.

U.S. Pat. No. 3,964,484 also describes a suction canula for autotransfusion during surgery which seeks to maintain a constant anticoagulant to aspirated blood volume ratio. This canula has a suction nozzle at one end and the opposite end is connected by a flexible tube to a blood storage vessel depressurised by a vacuum source. The canula also has an air vent and is connected to an anticoagulant feed passage which opens into the canula near the suction nozzle. The anticoagulant feed passage includes a valve to shut off the passage if the canula is not depressurised and to open it when the canula is depressurised. To this end the valve includes a flexible, elastic diaphragm communicating on one side with the interior of the canula and having the other side pressed elastically against a plate onto which the anticoagulant feed passage opens. If the canula is aspirating air through the suction nozzle and/or through the vent the pressure drop inside it is small and the flexible diaphragm of the valve remains elastically pressed against the plate and shuts off the anticoagulant feed passage. When the user shuts off the air vent and immerses the suction nozzle in blood the latter is aspirated and the resulting pressure drop in the canula causes the flexible diaphragm to be lifted away from the plate to open the anticoagulant feed circuit.

This suction canula also has its drawbacks:

1. When blood is not being aspirated the canula aspirates air continuously and this air enters the blood storage vessel, causing the problems mentioned above.

2. While blood is being aspirated the suction canula may be totally or partly blocked, by various kinds of debris, for example; the user cannot detect this immediately and there may therefore be a period in which anticoagulant is aspirated but no blood, or less blood; this may make the blood already aspirated unusable for the reasons explained above.

SUMMARY OF THE INVENTION

An object of the present invention is to provide a suction device for autotransfusion during surgery which firstly guarantees that the anticoagulant is mixed with the blood with the ratio of the volume of anticoagulant to the volume of blood within a given range of values and secondly does not degrade the blood collected.

The present invention consists in a suction device for autotransfusion during surgery comprising a suction canula having a tubular suction nozzle communicating with an interior passage of said canula, said passage of the canula being connected to a blood collection storage vessel adapted to be depressurised by a vacuum source, said passage of the canula communicating with an anticoagulant feed circuit incorporating an anticoagulant feed control valve, characterized in that:

—said device includes an independent vacuum circuit adapted to aspirate only air and connected to the vacuum source, to the blood collection storage vessel and to the valve, —the valve includes a vacuum chamber connected to said vacuum circuit, said vacuum chamber having a deformable wall connected to a closure member of the anticoagulant circuit adapted to shut off the anticoagulant feed circuit and said closure member being urged towards a closed position by elastic means and adapted to be urged towards an open position by deformation of said deformable wall when there is a sufficient pressure drop in the vacuum chamber, and —the vacuum circuit communicates with an air vent adapted to be shut off manually.

The invention further consists in a suction canula for autotransfusion during surgery comprising a canula body forming a sleeve and having a tubular suction nozzle communicating with an interior passage of said canula, said passage of the canula being connected to a blood collection storage vessel adapted to be depressurised by a vacuum source, said passage of the canula communicating with an anticoagulant feed passage incorporating an anticoagulant feed control valve, characterized in that:

—said canula includes an independent vacuum passage adapted to aspirate only air connectable to the vacuum source and connected to the valve, —the valve includes a vacuum chamber connected to said vacuum passage, said vacuum chamber having a deformable wall connected to a closure member of the anticoagulant passage adapted to shut off the anticoagulant feed passage and said closure member being urged towards a closed position by elastic means and adapted to be urged towards an open position by deformation of said deformable wall when there is a sufficient pressure drop in the vacuum chamber, and —the vacuum passage communicates with an air vent adapted to be shut off manually.

At least part of the canula is advantageously transparent so that a user can see the blood flowing in said canula.

In one advantageous embodiment of the invention the closure member of the anticoagulant passage is movable between its closed position and a maximally open position to define an anticoagulant flow cross-section which varies continuously between zero and a maximal value.

Said elastic means of the valve advantageously comprises a compression spring in the vacuum chamber, and the valve includes means for adjusting the compressive force of the spring.

In one embodiment of the invention said deformable wall of the vacuum chamber has a first side communicating with the vacuum chamber and a second side communicating with the anticoagulant feed circuit. The anticoagulant feed passage closure member is advantageously made from an elastomer material, and the deformable wall of the vacuum chamber is advantageously a flexible wall formed integrally or in one piece with the anticoagulant feed passage closure member.

In another embodiment of the invention:

—the closure member of the anticoagulant passage is fastened to a closure member of the air vent, —both closure members are movable between a rest position in which the anticoagulant passage closure member shuts off said anticoagulant passage and the air vent closure member opens the air vent and a forced active position in which the anticoagulant feed passage closure member opens said anticoagulant feed passage to the maximum and the air vent closure member shuts off the air vent, —both closure members are mechanically coupled to actuator means for moving the two closure members between their rest and forced active positions.

Advantageously, said deformable wall of the vacuum chamber has a first side communicating with the vacuum chamber and a second side open to the atmosphere and the canula further comprises a deformable wall of the anticoagulant circuit having a first side communicating with the anticoagulant circuit and a second side open to the atmosphere, said deformable wall of the anticoagulant circuit being also fastened to the two closure members, and said actuator means comprise a lever connected to the two closure members by first articulation means disposed between the two deformable walls and said lever is connected to the body of the canula by second articulation means, said lever also having one end projecting from the body of the canula. In this case, in one embodiment of the invention, the two closure members are connected by a rod having a cross-section smaller than that of the closure members and said first articulation means of the lever comprise a fork engaged with said rod.

Advantageously:

—the body of the canula includes a sleeve having a front end and a valve assembly fixed to the front end of the sleeve, said valve assembly including a base body, an intermediate ring and a valve body in a stacked arrangement, —the two closure members and the rod connecting them move axially in a cylindrical recess extending through the intermediate ring, —the intermediate ring includes a lateral window through which the cylindrical recess of said intermediate ring is open to the atmosphere, and —the lever is moulded in one piece with said intermediate ring, said lever passes through said lateral window and said second articulation means comprise two bridges of material between the lever and the intermediate ring.

In one embodiment of the invention, the anticoagulant feed passage closure member is made from an elastomer material, the deformable wall of the anticoagulant circuit is a flexible wall in one piece with the anticoagulant feed passage closure member, the air vent closure member is made from an elastomer material, the deformable wall of the vacuum chamber is a flexible wall in one piece with the air vent closure member, the deformable wall of the anticoagulant circuit has an outer peripheral edge trapped between the base body and the intermediate ring and the deformable wall of the vacuum chamber has an outer peripheral edge trapped between the valve body and the intermediate ring.

BRIEF DESCRIPTION OF THE DRAWINGS

In the drawings:

—FIG. 1 shows one embodiment of a canula of the device in accordance with the invention in partial longitudinal cross-section on the line I—I in FIG. 3, —FIG. 2 shows the canula from FIG. 1 from above in partial cross-section on the line II—II in FIG. 1, —FIG. 3 is a rear view of the canula from FIG. 1 as seen in the direction of the arrow III in FIG. 1, —FIG. 4 is a perspective view of one embodiment of static mixer that can be used in the canula from FIG. 1, —FIG. 6 is a diagram showing the connection of the canula from FIG. 1 to a vacuum circuit, to a blood storage vessel and to an anticoagulant storage vessel, —FIG. 7 is a view similar to FIG. 2 showing an alternative embodiment of the canula from FIGS. 1 to 6, —FIG. 8 is a view similar to FIG. 1 showing another embodiment of the canula of the device in accordance with the invention, —FIG. 9 shows part of the canula from FIG. 8 to a larger scale to show the details of its valve, —FIG. 10 shows the canula from FIGS. 8 and 9 in cross-section on the line X—X in FIG. 9, —FIG. 10a is a view in cross-section on the line A—A in FIG. 10, and —FIG. 11 is a detail view in partial cross-section showing the closure member of the valve from FIG. 9.

DETAILED DESCRIPTION OF THE PREFERRED EMBODIMENTS

Figure 5:
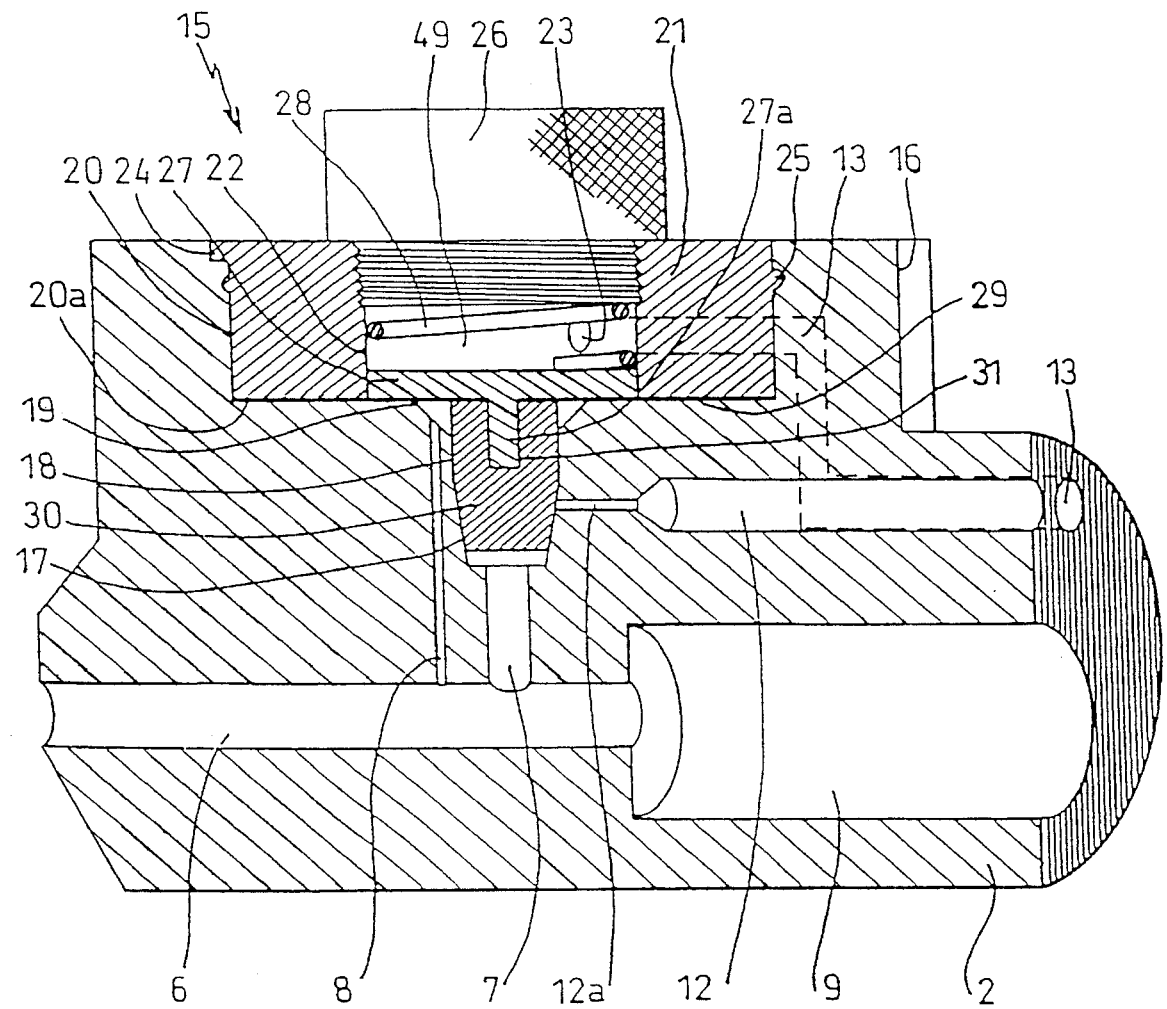
—FIG. 5 is a perspective view showing the canula from FIG. 1 in more detail and in cross-section on the line V—V in FIG. 2.

Referring to FIG. 1, the suction device in accordance with the invention includes a suction canula 1. The canula 1 includes a sleeve 2 extending between a front end 3 and a rear end 4. For reasons that become clear below, the sleeve 2 is advantageously made from a transparent material, normally a plastics material.

The front end 3 is extended by a suction nozzle 5 used to aspirate blood lost during surgery and normally made from plastics material, in the form of a tubular conduit which curves downwardly in the normal position in which the canula is used. The suction nozzle 5 can be in one piece with the sleeve 2, for example moulded in one piece with it and then curved to shape. The suction nozzle 5 can instead be a separate part which is inserted into the front end 3 of the sleeve 2: a seal is then provided between the sleeve 2 and the suction nozzle 5 by peripheral rings on the outside of the suction nozzle which snap into complementary grooves on the sleeve 2, for example, or by O-rings between the two parts, or by any other known means; this means that the surgeon can select a suction nozzle 5 whose shape is suited to the type of surgical procedure to be undertaken. The nozzle 5 can be permanently fixed (e.g. glued) to the sleeve 2. The suction nozzle 5 is itself advantageously made from a transparent material.

Inside the sleeve 2 the suction nozzle communicates with a longitudinal suction passage 6 which in turn communicates with an anticoagulant feed passage 7 and a secondary passage 8. The suction passage 6 is extended as far as the rear end 4 of the sleeve 2 by a mixing chamber 9. The suction passage 6 can be cylindrical with substantially the same inside diameter as the suction nozzle 5 or conical, converging towards the chamber 9, for reasons that emerge below, or any other shape.

The mixing chamber 9 can be a cylindrical longitudinal cavity open at the rear end 4 of the sleeve and with a diameter greater than that of the suction passage 6. The mixing chamber 9 includes a static mixer 10 which is helical in this specific example. Alternatively, as shown in FIG. 4, the static mixer 10 can be made up of plane surfaces divided into two sets separated by a plane containing the axis of the cylindrical chamber 9: a first set of parallel surfaces 10a at an angle a to the axis of the chamber 9 and a second set of parallel surfaces 10b not parallel to the surfaces 10a, being at the same angle α to the axis of the chamber 9, for example. The static mixer 10 can be of any other kind provided that it creates turbulence in the flow of blood and anticoagulant from the suction passage 6 in order to mix them homogeneously. The mixer 10 can instead be a non-static mixer, for example a helical screw rotated by the flow of blood.

Examples of static mixers are given in U.S. Pat. Nos. 3,964,484, 3,955,573 and 4,002,170.

The rear end of the mixing chamber 9 is fitted with an end-piece 11 which holds the static mixer 10 in the chamber 3 and also connects the chamber 9 to a flexible tube (not shown) for conveying aspirated blood to a storage vessel. The end-piece 11 can be fixed to the sleeve 2 by any means, for example screwing, force-fitting, snap-fastening, etc. The end-piece 11 can feasibly be dispensed with, in which case the static mixer 10 can be held in the chamber 9 by friction, gluing, welding or any other means, and the flexible tube for the aspirated blood can be connected directly to the chamber 9.

Referring to FIGS. 2 and 3, the sleeve 2 also includes two longitudinal passages which open at its rear end 4: a vacuum passage 13 whose rear end is connected by a flexible tube (not shown) to a vacuum source, and an anticoagulant feed passage 12 whose rear end connects via a flexible tube (not shown) to an anticoagulant storage vessel. As shown in FIG. 1, the vacuum passage 13 communicates with an air vent 14 in the upper part of the sleeve 2 of the canula 1. Both passages 12 and 13 also extend towards an anticoagulant feed control valve 15 described in detail below.

As shown in FIG. 5, the valve 15 is housed in a cylindrical protrusion 16 of the sleeve 2 which projects above the sleeve 2 when the canula 1 is in its position of use, said protrusion 16 being substantially perpendicular to the longitudinal axis of the sleeve 2 and centred on the anticoagulant feed passage 7 already described. The passage 7 opens into the suction passage 6 perpendicularly thereto. The passage 7 extends a certain distance towards the protrusion 16 and then widens in the upward direction to form a frustoconical valve seat 17. The valve seat 17 is extended upwards by a cylindrical bore 18 and then by a taper 19 which opens into a cylindrical or other shape recess 20 to form a shoulder 20a. The recess 20 has its open side at the top of the protrusion 16. The anticoagulant feed passage 12 is extended by a smaller cross-section portion 12a which opens into the frustoconical valve seat 17 substantially perpendicular to its axis. The cross-section of the portion 12a is such that when the valve seat 17 is not shut off and blood is aspirated into the passage 6 due to the depressurization, anticoagulant is aspirated through the portion 12a and the passage 7 at a rate such that it is mixed with the blood with a ratio of the volume (or flowrate) of the anticoagulant to the volume (or flowrate) of the blood in a predetermined range of values. With an anticoagulant such as heparin or CPD (citrate-phosphate-dextrose) the ratio of the volume (or flowrate) of the anticoagulant to the volume (or flowrate) of the blood should be between 1:10 and 1:5 and preferably around 1:7. With other anticoagulants the range of permissible values can be different. The vacuum passage 13 opens into the recess 20 and the auxiliary passage 8 joins the taper 19 to the suction passage 6.

A ring 21 whose shape is complementary to that of the recess 20 is a fluid-tight fit in said recess 20. The ring 21 is normally made from a synthetic material. The ring 21 has at its center a cylindrical bore 22 whose upper part is screwthreaded and it also has a radial passage 32 through it below the threaded portion and communicating with the vacuum passage 13 when the ring 21 is fitted into the recess 20. If the exterior shape of the ring 21 is that of a body of revolution, it advantageously has a lug 24 on the outside cooperating with a complementary shaped recess of the protrusion 16 to locate the radial passage 23 in corresponding relationship to the outlet from the vacuum passage 13 into the recess 20. The ring 21 can be fixed into the recess 20 by snapping a peripheral ring 25 on the outside of the ring 21 into a complementary shape groove in the recess 20. The ring 25 can be replaced with a peripheral O-ring engaged in a peripheral groove in the recess 20 and a corresponding peripheral groove in the ring 21. The ring 21 can also be fixed permanently, for example glued, into the recess 20. A knurled head screw 26 is screwed into the screwthreaded part of the central bore 22 in the top part of the ring 21. Also, a bearing disc 27 is slidably mounted in the central bore 22 and includes a central rod 27a extending towards the valve seat 17. A coil spring 28 is disposed between the bearing disc 27 and the knurled head screw 26 to urge the bearing disc 27 towards the shoulder 20a.

A flexible elastic diaphragm 29 is disposed between the ring 21 and the shoulder 20a. This diaphragm can simply be gripped between the ring 21 and the shoulder 20a or it can be glued to the ring 21. The diaphragm 29 can be made from latex, for example. The ring 21, the screw 26 and the diaphragm 29 define a vacuum chamber 49 communicating only with the vacuum passage 13.

The valve 15 includes a valve stem 30 having a frustoconical part adapted to seat in a fluid-tight manner on the valve seat 17 to shut off the portion 12a of the anticoagulant feed passage 12 and a cylindrical part adapted to slide in the cylindrical bore 18 to guide said valve stem 30. The cylindrical bore 18 and the cylindrical part of the valve stem 30 can be dispensed with without departing from the scope of the present invention. The valve stem 30 also has a central bore 31 into which the rod 27a of the bearing disc 27 is forced, though the diaphragm 29. The valve stem 30 is therefore fastened to the central part of the diaphragm 29 and the bearing disc 27.

FIG. 6 shows the connection of the suction canula 1 to the vacuum source 40, to the blood storage vessel 41 and to the anticoagulant storage vessel 42. The vacuum source 40 can be just a valve connected to a vacuum circuit connected to a vacuum pump or to some other suction system and connected by a flexible tube 50 to a Tee connector 45 which connects it to the collected blood storage vessel 41 via a flexible tube 43 and to the vacuum passage 13 of the canula 1 via a flexible tube 44 connected to the rear end 4 of the sleeve 2.

The storage vessel 41 for collected blood can in the conventional way have a rigid outer casing containing a flexible sachet in which the blood is collected, the outer casing and the flexible sachet both being connected to the flexible tube 43. The pressure drop at the vacuum source 40, as measured by a pressure gauge 40a, can be in the order of 30 mm to 60 mm of mercury, preferably 30 mm to 40 mm of mercury, to prevent corpuscular trauma.

The blood collection storage vessel 41, to be more precise the flexible sachet in which the blood is collected, is connected to the mixing chamber 9 of the canula 1 by a flexible tube 46. The storage vessel 41 usually incorporates a filter to hold back any debris aspirated with the blood. The filter can have a mesh size of 150 μm to 170 μm, for example. The storage vessel 41 is designed in the known way to prevent blood being aspirated out of it towards the vacuum source 40.

Examples of blood storage vessels that can be used in the device of the present invention are described in U.S. Pat. No. 3,866,608 (equivalent to French patent 2,248,424) and U.S. Pat. No. 3,680,560 (equivalent to Belgian patent 753,552).

The anticoagulant storage vessel 42 is connected by a flexible tube 47 to the anticoagulant feed passage 12 of the canula 1. The anticoagulant can be heparin, CPD (citrate-phosphate-dextrose), a mixture of heparin and CAD (citric acid-dextrose), etc.

The suction canula operates as follows: if the air vent 14 of the vacuum passage 13 is open air is aspirated towards the vacuum source 40 through the vent 14, the passage 13 and the tube 44. There is therefore a very small pressure drop in the flexible tube 43 and in the storage vessel 41 in which the blood is collected, and no suction through the tube 46, the chamber 9, the passage 6 and the suction nozzle 5. There is no or very little pressure drop in the part of the vacuum passage 13 between the air vent 14 and the valve 15. The pressure drop in the vacuum chamber 49 is therefore too small for the diaphragm to be lifted off the bearing disc 27 and the valve stem 30; the frustoconical valve stem 30 is therefore held seated in a fluid-tight manner on the valve seat 17 by the spring 28 and the section 12a of the passage 12 remains shut off.

Thus, provided the air vent 14 is open, there is no suction via the suction nozzle 5 of the canula 1, the canula is not fed with anticoagulant and no air enters the collected blood storage vessel 41. This prevents haemolysis and pollution of the blood in the storage vessel 41.

If the user blocks the air vent 14 with a finger when the suction nozzle 5 of the canula is not immersed in a liquid, air is aspirated by the vacuum source 40 via the suction nozzle 5, the passage 6, the mixing chamber 9, the flexible tube 46, the blood collection storage vessel 41 and the tube 43. This causes air to enter the blood collection storage vessel 41 but does not represent normal use of the suction canula: the user normally blocks the vent 14 only after immersing the suction nozzle 5 in the blood to be aspirated, i.e. air enters the blood collection storage vessel only under exceptional circumstances. The flow of air produces only a small head loss: there is thus a small pressure drop at the Tee connector 45 and therefore in the flexible tube 44, the vacuum passage 13 of the canula 1 and in the vacuum chamber 49 of the valve. The force of the spring 28 is therefore sufficient to counteract this small pressure drop and the valve stem 30 continues to be pressed against the valve seat 17 and the anticoagulant feed passage 12 remains shut off. Thus suction of air with no suction of blood does not lead to suction of anticoagulant. There is therefore no risk of the blood already collected deteriorating due to the suction of massive amounts of anticoagulant.

If the user blocks the vent 14 after immersing the suction nozzle 5 of the canula in the blood escaping during the surgical procedure the pressure drop caused by the vacuum source 40 aspirates blood into the collection storage vessel 41.

The flow of blood in the canula 1 and the tube 46 causes a large head loss and the pressure drop in the tube 43, the connector 45, the tube 44, the vacuum passage 13 and the vacuum chamber 49 is similar to that due to the vacuum source 40, which is sufficient to counteract the force of the spring 28 of the valve 15. The elastic diaphragm 29 is therefore raised with the bearing disc 27 and the valve stem 30 which is therefore lifted off the valve seat 17: the anticoagulant feed passage 12 is no longer shut off and due to the pressure drop in the suction passage 6 the anticoagulant can flow from the storage vessel 42 via the tube 47, the passage 12 and its smaller cross-section portion 12a and the anticoagulant feed passage 7 into the suction passage 6 where it begins to mix with the aspirated blood. The mixture is homogenized in the mixing chamber 9 by the static mixer 10. The diaphragm 29 prevents the anticoagulant from being aspirated into the vacuum circuit.

If air bubbles are aspirated with the blood the pressure drop in the vacuum chamber 49 is reduced: the spring 28 therefore tends to push the valve stem 30 towards the valve seat 17, but without it coming into contact with the seat 17: because the stem 30 and the seat 17 are frustoconical the anticoagulant flow cross-section between the stem 30 and the seat 17 is reduced and the flowrate of the anticoagulant into the suction passage 6 is reduced. The aspirated blood flowrate is also diminished because of the aspirated air, and the ratio of the flowrate of anticoagulant to the flowrate of blood in the mixture of anticoagulant and blood therefore remains in the range of acceptable values defined above. The user can turn the knurled head screw 26 to adjust the compression force of the spring 28 and so vary the anticoagulant flowrate.

If the suction nozzle 5 is blocked by aspirated debris or for any other reason, suction of blood stops or continues at a reduced rate: as the canula is transparent the user can easily see that this has happened. The flow of the blood can be seen because of the air bubbles or bone or tissue debris aspirated along with the blood and any major change in the concentration of anticoagulant in the aspirated blood or the suction of anticoagulant only changes the color of the aspirated liquid in the canula. The user can therefore react quickly and stop suction in order to clear or change the suction canula.

The knurled head screw 26 can be dispensed with without departing from the scope of the invention. Likewise the valve stem 30 and the valve seat 17 can be cylindrical rather than frustoconical, although this is not preferred as in this case the flowrate of anticoagulant is not varied according to the blood flowrate as when the valve stem is frustoconical and the portion of the passage 12 is either shut off or open. The diaphragm 29 can be replaced by a piston sliding in and sealed to the bore 22: the disc 27 can function as this piston if its upward travel is limited so that it cannot rise above the passage 23, as in this case anticoagulant can be aspirated into the vacuum circuit. If the diaphragm is dispensed with the disc 27 can be in one piece with the valve stem 30.

The passage 6 can have a conical shape that converges towards the chamber 9: the Venturi effect then increases the pressure drop in the passage 6 at the anticoagulant feed passage 7, facilitating the suction of anticoagulant.

When the user stops blocking the air vent 14 suction of blood ceases and the pressure drop in the vacuum chamber 49 is eliminated, as a result of which the spring 28 pushes the bearing disc 27, the diaphragm 19 and the valve stem 30 towards the valve seat 17 until said stem 30 is pressed onto said seat 17 and shuts off the anticoagulant feed passage 12: the flow of anticoagulant therefore ceases. If anticoagulant has collected between the diaphragm 29 and the shoulder 20a is collected in the taper 19 and evacuated to the passage 6 via the auxiliary passage 8: for this reason it does not impede the closing of the valve 15.

FIG. 7 shows an alternative embodiment of the canula in accordance with the invention which has an additional passage 48 communicating with the vacuum passage 13 and connected to the blood collection storage vessel 41. The tube 50 and the Tee connector 45 of FIG. 6 are dispensed with, the tube 44 connects the passage 13 direct to the vacuum source 40 and the tube 43 connects the passage 48 to the blood collection storage vessel 41. The air vent 14 can be either on the passage 13 or on the passage 48. The device operates in the same way as described above.

FIGS. 8 through 11 show another embodiment of the canula according to the invention. The structure and operation of this canula are similar to those of the canula from FIGS. 1 to 7 and therefore need not be described again in detail here. Components similar or identical to those of FIGS. 1 through 7 carry the same reference numbers as in FIGS. 1 through 7 increased by 100.

Referring to FIG. 8, the canula 101 includes a sleeve 102 made from polystyrene, for example, extending longitudinally between a front end 103 and a rear end 104. A vacuum passage 113, an anticoagulant passage 112 and a mixing chamber 109 extend longitudinally through the sleeve 102. At the rear end 104 of the sleeve 102 the vacuum passage 113 is adapted to be connected to a flexible tube (not shown) connected to a vacuum source, the anticoagulant feed passage 112 is adapted to be connected to a flexible tube (not shown) connected to an anticoagulant storage vessel and the mixing chamber 109 is adapted to be connected to a flexible tube (not shown) connected to a storage vessel in which the blood is collected. The mixing chamber 109 contains a static mixer 110 as described above which can also be made from polystyrene and which is merely nested inside the chamber 109. The mixing chamber 109 advantageously has a smaller inside diameter rear end 109a to hold the mixer 110 in place. The canula 101 includes a valve assembly 151 fixed to the front end 103 of the sleeve 102 and described in more detail below. The valve assembly 151 has a front end 151a and a rear end 151b. It contains a valve 115 for controlling the supply of anticoagulant.

A blood suction tube or nozzle 105 and an anticoagulant feed tube 107 parallel to it extend towards the front from the valve assembly 151. The two tubes are interconnected at their front end by a suction end-piece 152. The end-piece 152 can include an inlet orifice 153 and two orifices 154, 155 respectively receiving the tubes 105 and 107. The end-piece 152 and the two tubes 105 and 107 can be made from PVC, for example. Both tubes 105 and 107 can be force fitted, glued or fixed in any other way into the end-piece 152.

As shown in FIG. 9 the valve assembly 151 includes three stacked parts: a base body 156 at the bottom, an intermediate ring 157 and a valve body 158 at the top. These three parts are assembled together by any known means, for example by screws 159 which pass through the valve body 158 and the ring 157 into the base body 156. In the example shown the base body 156 and the valve body 158 are moulded from polystyrene and the intermediate ring 157 is moulded from acetal resin.

A suction passage 106 passes longitudinally through the lower part of the base body 156. The suction passage 106 extends between a front end 106a which communicates with the blood suction tube 105 and a rear end 106b which communicates with the mixing chamber 109. The blood suction tube 105 is force-fitted or glued into the front end 106a of the passage 106. The rear end 106b of the passage 106 forms an end-piece 160 which is nested in the mixing chamber 109. The end-piece 160 is fixed into the mixing chamber 109 by any known means such as force-fitting or glueing, for example. The end-piece 160 also helps to retain the static mixer 110 in the mixing chamber 109.

The base body 156 also has an upper surface 161 on which a cylindrical cup 162 is formed. A cylindrical recess 163 at the center of the cylindrical cup 162 is extended downwardly by a conical recess 164. The cylindrical recess 163 has a wider upper part 163a for reasons to be explained below.

The base body 156 also includes a passage 112a extending between a rear end 112b communicating with the anticoagulant feed passage 112 and a smaller cross-section front end 112c which opens into the conical recess 164. The rear end 112b of the passage 112a forms an end-piece 165 which is nested in the passage 112. The end-piece 165 can be force-fitted or glued into the passage 112.

The base body 156 further includes a passage 166 extending between a front end 166a into which the anticoagulant feed tube 107 opens and a rear end 166b which opens into the lower part of the conical recess 164. The anticoagulant feed tube 107 can be fixed into the passage 166 by any known means such as force-fitting or glueing, for example. In the example shown, for reasons explained below, the rear end 166b of the passage 166 must open into the conical recess 164 at a position below the position of the front end 112c of the passage 112a.

The ring 157 has a lower surface 167 and an upper surface 168. A cylindrical recess 169 extends vertically through it between its upper surface 168 and its lower surface 167. The lower surface 167 of the ring 157 has a cylindrical projecting part 170 adapted to nest in the cup 162 of the base body. The upper surface 168 of the ring 157 incorporates a cylindrical cup 171 similar to the cup 162 of the base body.

As shown in FIGS. 10 and 10a, the ring 157 includes a lateral window 172 through which passes a lever 173. The lever 173 extends between an outside end 174 and a forked inside end 175, the utility of which is explained below. The lever 173 is joined to the ring 157 by two bridges 176 of material extending laterally to each side of the lever 173, and advantageously made from acetal resin. When a user presses the outside end 174 of the lever vertically downwards, as explained below, the material bridges 176 are deformed elastically in torsion and when the user releases the lever the elasticity of the material bridges 176 returns the lever 173 to its original position.

Referring to FIG. 9, the valve body 158 has an upper surface 177 and a lower surface 178. The lower surface 178 incorporates a cylindrical projection 179 adapted to nest in the cylindrical cup 171 of the ring 157. The valve body 158 includes a cylindrical recess 180 aligned with the cylindrical recess 169 of the ring 157 and extending some distance from the lower surface 178 of the valve body. The upper surface 177 of the valve body includes an air vent 114 communicating with the cylindrical recess 180 of the valve body via a frustoconical valve seat 181. The valve body 158 includes a passage 113a extending between a rear end 113b communicating with the vacuum passage 113 and a front end 113c opening into the cylindrical recess 180, said cylindrical recess 180 thus forming a vacuum chamber 149. The rear end 113b of the passage 113a forms an end-piece 182 which enters the passage 113. The end-piece 182 can be fixed into the passage 113 by any known means such as force-fitting or glueing, for example.

A valve assembly 183 is disposed inside the cylindrical recesses 180 and 169. Referring to FIG. 11, the valve assembly 183 is made up of two sealing members 184, 185 joined together by a connecting rod 186. The two sealing members 184, 185 are moulded from an elastomer material and are advantageously identical. The sealing member 184 has a cylindrical part 187a extending axially between a rear end 188a and a conical front end 189a. The conical front end advantageously includes a peripheral lip seal 190a. The rear end 188a incorporates a cylindrical recess 191a. At an intermediate position along the length of the cylindrical part 187a the sealing member incorporates an outer ring 192a extended outwards by a thin annular flange 193a. Because it is thin the flange 193a is flexible and it is advantageously formed with at least one annular corrugation 194a for reasons explained below. The sealing member 185 is identical to the sealing member 184 and its various component parts are identified by the same reference numbers as the component parts of the sealing member 184 with the suffix "b" instead of the suffix "a". In the embodiment of FIGS. 1 through 7 the closure member and the flexible diaphragm can be replaced with a sealing member similar to the sealing member 184. The rod 186, which can be moulded from polystyrene, is nested in the recesses 191 of the two sealing members 184, 185 and is fixed to the sealing members by any known means such as force-fitting or glueing, for example.

As shown in FIG. 9, the outside edge 195a of the sealing member 184 is gripped all around its perimeter between the bottom of the cup 162 and the cylindrical part 170 and the outside edge 195b of the thin wall of the upper sealing member 185 is gripped all around its perimeter between the bottom of the cup 171 and the cylindrical part 179. The upper sealing member 185 therefore forms a seal between the vacuum chamber 149 and the recess 168 in the ring 157. Likewise, the lower sealing member 184 forms a seal between the recess 168 in the ring 157 and the anticoagulant feed circuit.

A frustoconical spring 128 is disposed in the vacuum chamber 149. The spring 128 bears on the ring 192b of the upper sealing member 185 which urges the valve assembly 183 downwards. Thus when in the rest position, as shown in FIG. 9, the lip seal 190 of the lower sealing member 184 is pressed against the surface of the frustoconical recess 164, at a point above the end 166b of the passage 166 and below the end 112c of the passage 112a. The lower sealing member 184 in the rest position therefore shuts off the anticoagulant feed passage 112. In this rest position the two branches of the fork 175 of the lever 173 are disposed one on each side of the connecting rod 186 of the valve assembly 183 and the branches of the fork 175 are a small distance below the rear end 188 of the upper sealing member 185. The purpose of the wider upper portion 163a of the cylindrical recess 163, already described, is simply to prevent interference between the ring 192a and the intermediate ring 157.

If a user blocks the air vent 114 with his or her finger while the canula is in use blood and anticoagulant are aspirated in the same way as by the canula of FIGS. 1 to 7. There is sufficient clearance between the fork 175 and the rear end 188 of the lower sealing member 184 to allow free movement of the valve assembly 183 without interfering with the lever 173. The corrugations 194a and 194b in the flanges 193a and 193b allow easy axial displacement of the valve assembly 183.

If the user requires to aspirate blood and anticoagulant at the maximum flowrate at the same time without using the self-regulating feature of the canula in accordance with the present invention he or she can depress the outside end of the lever 174. The fork 175 then presses upwardly on the valve assembly 183 so that the upper sealing member blocks the air vent 114 by pressing the lip seal 190 against the valve seat 181 and the lower sealing member 184 is moved as far as possible from its rest position to allow the anticoagulant to flow at the maximum flowrate. As shown in FIG. 10, the outside end 174 of the lever 173 is advantageously on the lefthand side of the canula so that the user can easily operate the lever 173 with his or her thumb while holding the canula in his or her right hand.

The device in accordance with the invention has been tested by the inventor, without retransfusion, on a sample of 15 persons, five males and ten females. The average age of the subjects was 57 (age range from 18 to 86 years).

Table 1 below lists the surgical procedures carried out on the patients.

TABLE 1

| | |
|---|---|
| long saphenous vein removal | 2 |
| femoropopliteal bypass | 2 |
| aorto-bifemoral bypass | 2 |
| restoration of vascular flow | 4 |
| endoluminal angioplasty | 2 |
| splenectomy | 1 |
| cholecystectomy | 1 |
| bypass | 1 |

The average quantity of blood recovered was 540 cm$^3$ (range from 100 to 650 cm$^3$).

The plasma haemoglobin level was measured in samples of blood recovered from each patient by the device in accordance with the invention (referred to hereinafter as "autotransfused blood"). Table 2 below summarizes the results.

TABLE 2

| Patient | Plasma haemoglobin (g/dl) |
|---|---|
| 1 | 0.5 |
| 2 | 0.3 |
| 3 | 0.4 |
| 4 | 0.6 |
| 5 | 0.4 |
| 6 | 0.3 |
| 7 | 0.3 |
| 8 | 0.6 |
| 9 | 0.6 |
| 10 | 0 |
| 11 | coagulation |
| 12 | 0.1 |
| 13 | 0.3 |
| 14 | 0.2 |
| 15 | 0.4 |
| Average | 0.3 |

Fibrin deterioration products (FDP) were measured for 14 autotransfused blood samples from 14 patients (patients 1 to 10 and 12 to 15).

Table 3 below gives the number of samples corresponding to various ranges of FDP values.

TABLE 3

| FDP (µg/l) | Number of samples |
|---|---|
| <10 | 2 |
| 1–20 | 1 |
| 20–40 | 1 |
| 40–80 | 2 |
| 80–160 | 1 |
| 160–320 | 2 |
| 320–640 | 3 |
| 640–2 560 | 2 |
| Total | 14 |

Table 4 below gives the breakdown of 15 autotransfused blood samples from 15 patients as a function of the measured level of heparin in the samples.

TABLE 4

| Heparin (U/ml) | Number of samples |
|---|---|
| <0.05 | 4 |
| 0.09 | 1 |
| 0.28 | 1 |
| 0.40 | 1 |
| 0.41 | 1 |
| 0.7 | 1 |
| >0.7, <0.8 | 3 |
| >0.8 | 1 |
| coagulation | 1 |
| 0.1 (uncontrolled coagulation) | 1 |
| Total | 15 |

Table 5 below gives the breakdown of 15 autotransfused blood samples from 15 patients as a function of the measured prothrombin level (PL) of these samples.

TABLE 5

| PL (%) | Number of samples |
|---|---|
| <10 | 9 |
| 13 | 1 |
| 26 | 1 |

TABLE 5-continued

| PL (%) | Number of samples |
|---|---|
| 42 | 1 |
| 44 | 1 |
| 59 | 1 |
| coagulation | 1 |
| Total | 15 |

Table 6 below compares various measurements on 15 blood samples from the 15 patients with 15 autotransfused blood samples from the same patients.

TABLE 6

| Parameter | Units | Patients | | Autotransfused blood samples | |
|---|---|---|---|---|---|
| | | Mean | Max–Min | Mean | Max–Min |
| Erythrocytes | $\times 10^6/mm^3$ | 4.27 | 3.44–5.25 | 2.45 | 0.47–4.46 |
| Leucocytes | $\times 10^3/mm^3$ | 9.05 | 5.4–23 | 5.67 | 1.9–12.7 |
| Hematocrit | % | 39.6 | 39.9–48 | 23.5 | 4.1–41.9 |
| Haemoglobin | g/dl | 13.31 | 11.5–15.8 | 7.72 | 1.6–13.5 |
| Platelets | $\times 10^3/mm^3$ | 294.9 | 154–513 | 89.4 | 20–196 |

There was little deterioration of the blood collected, which was relatively rich in platelets. Coagulation was not compromised and retransfusion could have been carried out without difficulty.

I claim:

1. Suction device for autotransfusion during surgery comprising a suction canula (1; 101) having a tubular suction nozzle (5; 105) communicating with an interior passage (6, 9; 106, 109) of said canula (1;101), said passage (6, 9; 106, 109) of the canula being connected to a blood collection storage vessel (41) adapted to be depressurized by a vacuum source (40), said passage (6, 9; 106, 109) of the canula communicating with an anticoagulant feed circuit (42, 47, 12, 12a, 15, 7; 112, 112a) incorporating an anticoagulant feed control valve (15; 115), characterized in that:
 —said control device includes an independent vacuum circuit (13, 44, 45, 50, 43; 113, 113a) adapted to aspirate only air and connected to the vacuum source (40), to the blood collection storage vessel (41) and to the control valve (15; 115)
 —the control valve (15; 115) includes a vacuum chamber (49; 149) connected to said vacuum circuit (13, 44, 45, 50, 43; 113, 113a), said vacuum chamber (49; 149) having a deformable wall (29; 193b) connected to a closure member (30; 184) of the anticoagulant circuit adapted to shut off the anticoagulant circuit (42, 47, 12, 12a, 15, 7; 112, 112a) and said closure member (30; 184) being urged towards a closed position by elastic means (28; 128) and adapted to be urged towards an open position by deformation of said deformable wall (29; 193b) when there is a sufficient pressure drop in the vacuum chamber (49; 149), and
 —the vacuum circuit (23, 13, 44, 45, 50, 43; 113, 113a) communicates with an air vent (14; 114) adapted to be shut off manually.

2. Suction canula for autotransfusion during surgery comprising a canula body (2; 102, 151) forming a sleeve and having a tubular suction nozzle (5; 105) communicating with an interior passage (6, 9; 106, 109) of said canula (1; 101), said passage (6, 9; 106, 109) of the canula being connected to a blood collection storage vessel (41) adapted to be depressurised by a vacuum source (40), said passage (6, 9; 106, 109) of the canula communicating with an anticoagulant feed passage (12, 12a; 112, 112a) incorporating an anticoagulant feed control valve (15; 115), characterized in that:
 —said canula includes an independent vacuum passage (13; 113, 113a) adapted to aspirate only air connectable to the vacuum source (40) and connected to the control valve (15; 115),
 —the control valve (15; 115) includes a vacuum chamber (49; 149) connected to said vacuum passage (13; 113, 113a), said vacuum chamber (49; 149) having a deformable wall (29; 193b) connected to a closure member (30; 184) of the anticoagulant passage adapted to shut off the anticoagulant feed passage (12, 12a; 112, 112a) and said closure member (30; 184) being urged towards a closed position by elastic means (28; 128) and adapted to be urged towards an open position by deformation of said deformable wall (29; 193b) when there is a sufficient pressure drop in the vacuum chamber (49; 149), and
 —the vacuum passage (13; 113, 113a) communicates with an air vent (14; 114) adapted to be shut off manually.

3. Canula according to claim 2 wherein at least part of the canula is transparent so that a user can see the blood flowing in said canula.

4. Canula according to claim 2 wherein the closure member of the anticoagulant passage (30; 184) is movable between its closed position and a maximally open position to define a cross-section of the anticoagulant passage which varies continuously between zero and a maximal value.

5. Canula according to claim 2 wherein said elastic means (28) of the control valve (15) comprises a compression spring (28) in the vacuum chamber (49) and the valve (15) includes means (26) for adjusting the compression force of the spring (28).

6. Canula according to claim 2 wherein said deformable wall (29) of the vacuum chamber has a first side communicating with the vacuum chamber and a second side communicating with the anticoagulant feed circuit.

7. Canula according to claim 2 wherein:
 —the closure member (184) of the anticoagulant passage is fastened to a closure member (185) of the vent (114),
 —both closure members are movable between a rest position in which the anticoagulant passage closure member (184) shuts off said anticoagulant passage and the air vent closure member (185) opens the air vent and a forced active position in which the anticoagulant feed passage closure member (184) opens said anticoagulant feed passage to the maximum and the air vent closure member (185) shuts off the air vent,
 —both closure members are mechanically coupled to actuator means (173) for moving the two closure members between their rest and forced active positions.

8. Canula according to claim 7 wherein said deformable wall (193b) of the vacuum chamber has a first side communicating with the vacuum chamber and a second side open to the atmosphere and the canula further comprises a deformable wall (193a) of the anticoagulant circuit having a first side communicating with the anticoagulant circuit and a second side open to the atmosphere, said deformable wall (193a) of the anticoagulant circuit being also fastened to the two closure members (184, 185), and said actuator means comprise a lever (173) connected to the two closure members by first articulation means (175) disposed between the two deformable walls and said lever (173) is connected to the body of the canula by second articulation means (176), said lever (173) also having one end (174) projecting from the body of the canula.

9. Canula according to claim 8 wherein the two closure members (184, 185) are connected by a rod (186) having a cross-section smaller than that of the closure members and said first articulation means of the lever (173) comprise a fork (175) engaged with said rod (186).

10. Canula according to claim 8 wherein:
—the body of the canula includes a sleeve (102) having a front end (103) and valve means (151) fixed to the front end of the sleeve, said valve means including a base body (156), an intermediate ring (157) and a valve body (158) in a stacked arrangement,
—the two closure members (184, 185) and the rod (186) connecting them move axially in a cylindrical recess (168) extending through the intermediate ring (157),
—the intermediate ring (157) includes a lateral window (172) through which the cylindrical recess (168) of said intermediate ring is open to the atmosphere,
—the lever (173) is moulded in one piece with said intermediate ring (157), said lever passes through said lateral window (172) and said second articulation means comprise two bridges of material (176) between the lever and the intermediate ring.

11. Canula according to claim 10 wherein the anticoagulant feed passage closure member (184) is made from an elastomer material, the deformable wall (193a) of the anticoagulant circuit is a flexible wall in one piece with the anticoagulant feed passage closure member (184), the air vent closure member (185) is made from an elastomer material, the deformable wall (193a) of the vacuum chamber is a flexible wall in one piece with the air vent closure member (185), the deformable wall (193a) of the anticoagulant circuit has an outer peripheral edge (195a) trapped between the base body (156) and the intermediate ring (157) and the deformable wall (193b) of the vacuum chamber has an outer peripheral edge trapped between the valve body (158) and the intermediate ring (157).

12. Canula according to claim 6 wherein the anticoagulant feed passage closure member (184) is made from an elastomer material and the deformable wall (193b) of the vacuum chamber is a flexible wall in one piece with the anticoagulant feed passage closure member (184).

* * * * *